US011633362B2

(12) United States Patent
Mørch et al.

(10) Patent No.: US 11,633,362 B2
(45) Date of Patent: Apr. 25, 2023

(54) SYSTEM FOR DELIVERY OF MEDICAL COMPONENTS TO THE LUNGS

(71) Applicant: SINTEF TTO AS, Trondheim (NO)

(72) Inventors: Yrr Mørch, Trondheim (NO); Einar Sulheim, Trondheim (NO)

(73) Assignee: SINTEF TTO AS, Trondheim (NO)

( * ) Notice: Subject to any disclaimer, the term of this patent is extended or adjusted under 35 U.S.C. 154(b) by 0 days.

(21) Appl. No.: 16/643,682

(22) PCT Filed: Sep. 5, 2018

(86) PCT No.: PCT/EP2018/073846
§ 371 (c)(1),
(2) Date: Mar. 2, 2020

(87) PCT Pub. No.: WO2019/048464
PCT Pub. Date: Mar. 14, 2019

(65) Prior Publication Data
US 2020/0268674 A1   Aug. 27, 2020

(30) Foreign Application Priority Data

Sep. 5, 2017   (NO) .................................. 20171436

(51) Int. Cl.
| | |
|---|---|
| *A61K 9/00* | (2006.01) |
| *A61K 9/51* | (2006.01) |
| *A61K 9/50* | (2006.01) |
| *A61K 45/06* | (2006.01) |
| *A61K 47/69* | (2017.01) |

(52) U.S. Cl.
CPC .......... *A61K 9/5073* (2013.01); *A61K 9/0073* (2013.01); *A61K 9/5146* (2013.01); *A61K 45/06* (2013.01); *A61K 47/6925* (2017.08)

(58) Field of Classification Search
None
See application file for complete search history.

(56) References Cited

U.S. PATENT DOCUMENTS 9,421,194 B2    8/2016  Prud'homme et al.
2001/0051131 A1*  12/2001  Unger .................. A61K 49/223
                                                  424/9.5

(Continued)

FOREIGN PATENT DOCUMENTS

EP          2913065 A1    9/2015
WO     WO-2014021678 A1 *  2/2014  .......... A61K 49/223

(Continued)

OTHER PUBLICATIONS

Graciela Mohamedi, Mehrdad Azmin, Isabel Pastoriza-Santos, Victoria Huang, Jorge Pérez-Juste, Luis M. Liz-Marzán, Mohan Edirisinghe, and Eleanor Stride. "Effects of Gold Nanoparticles on the Stability of Microbubbles." Langmuir, vol. 28, 2012, pp. 13808-13815. (Year: 2012).*

(Continued)

*Primary Examiner* — Isaac Shomer
(74) *Attorney, Agent, or Firm* — Fox Rothschild LLP (57) ABSTRACT

The present invention relates generally to pharmaceutical formulations. Particularly, the present invention relates to a new delivery system for delivery of medical components to the lungs, and its utility in the fields of pharmaceutical formulation, drug delivery, medicine and diagnosis.

26 Claims, 7 Drawing Sheets

Lungs from animals injected with A) PFC NP-MBs, B) PFC urea NP-MBs C) SF6 NP-MBs.

(56) References Cited

U.S. PATENT DOCUMENTS

| | | | | |
|---|---|---|---|---|
| 2003/0003055 | A1* | 1/2003 | Unger | A61K 41/0052 264/4.1 |
| 2010/0074927 | A1 | 3/2010 | Iversen et al. | |

FOREIGN PATENT DOCUMENTS

| | | |
|---|---|---|
| WO | 2014/191502 A1 | 12/2014 |
| WO | 2016/134115 A1 | 8/2016 |

OTHER PUBLICATIONS

Suntharavathanan Mahalingam, Bahijja Tolulope Raimi-Abraham, Duncan Q. M. Craig, and Mohan Edirisinghe. "Formation of Protein and Protein-Gold Nanoparticle Stabilized Microbubbles by Pressurized Gyration." Langmuir, vol. 31, 2015, pp. 659-666. (Year: 2015).*

Ýrr Mørch et al. "Nanoparticle-stabilized microbubbles for multimodal imaging and drug delivery." Contrast Media Molecular Imaging, vol. 10, 2015, pp. 356-366. (Year: 2015).*

E Stride and N Saffari. "Microbubble ultrasound contrast agents: a review." Proceedings of the Institution of Mechanical Engineers, Part H: Journal of Engineering in Medicine, vol. 217, 2003, pp. 429-447. (Year: 2003).*

Sunil Unnikrishnan and Alexander L. Klibanov. "Microbubbles as Ultrasound Contrast Agents for Molecular Imaging: Preparation and Application." American Journal of Roentgenology, vol. 199, Aug. 2012, pp. 292-299. (Year: 2012).*

Google Patents. English Translation of WO2014021678A1. Obtained from https://patents.google.com/patent/WO2014021678A1/en?oq=WO+2014%2f021678 on Jan. 10, 2022, originally published in Korean on Feb. 6, 2014, pp. 1-14. (Year: 2014).*

Afadzi M. et al., "Effect of Ultrasound Parameters on the Release of Liposomal Calcein", Ultrasound Med Biol. 2012;38:476-86.

Eggen S. et al., "Ultrasound Improves the Uptake and Distribution of Liposomal Doxorubicin in Prostate Cancer Xenografts", Ultrasound Med Biol. 2013;39:1255-66.

Xu R. et al., "An injectable nanoparticle generator enhances delivery of cancer therapeutics", Nat Biotechnol. 2016;34:414-8.

Gamucci O. et al., "Biomedical Nanoparticles: Overview of Their Surface Immune-Compatibility", Coatings. 2014;4:139-59.

Kumari A. et al., "Biodegradable polymeric nanoparticles based drug delivery systems", Colloids and Surfaces B: Biointerfaces. 2010;75:1-18.

Snipstad et al., "Ultrasound Improves the Delivery and Therapeutic Effect of Nanoparticle-Stabilized Microbubbles in Breast Cancer Xenografts", Ultrasound Med Biol. Nov. 2017;43(11):2651-2669.

Mørch, Y., et al., "Nanoparticle-stabilized microbubbles for multimodal imaging and drug delivery", Contrast Media & Molecular Imaging, 2015, vol. 10, p. 356-366.

Figueiredo, M. et al., "PLGA Nanoparticles for Ultrasound-Mediated Gene Delivery to Solid Tumors", Hindawi Publishing Corporation, Journal of Drug Delivery, vol. 2012, Article ID 767839, 20 pages.

Barrefelt, A., et al., "Biodistribution, kinetics, and biological fate of SPION microbubbles in the rat", International Journal of Nanomedicine, 2013:8 3241-3254.

Eggen Siv et al: "Ultrasound-enhanced drug delivery in prostate cancer xenografts by nanoparticles stabilizing microbubbles", Journal of Controlled Release, vol. 187, May 20, 2014, pp. 39-49.

* cited by examiner

Figure 1: Biodistribution of PACA NPs (control without microbubbles). 1-5: lung, liver, spleen, kidney and heart.

Figure 2: Biodistribution of PFC NP-MBs 30 min after injection. 1-5: lungs, liver, spleen, kidney, heart.

Figure 3: Biodistribution of air NP-MBs 30min after injections. 1-5: lungs, liver, spleen, kidney, heart.

Figure 4: Lungs from animals injected with; 1) Air NP-MBs, 2) NPs, 3) PFC NP-MBs.

Figure 5. Biodistribution of air-filled lipid-NP-MPs 30 min after injection. 1-4: lungs, liver, spleen, kidney.

Figure 6: Biodistribution of PACA air NP-MBs after 1h (A) and 2h (B). 1-3: lung, liver, spleen.

Figure 7: Lungs from animals injected with A) PFC NP-MBs, B) PFC urea NP-MBs C) SF6 NP-MBs.

SYSTEM FOR DELIVERY OF MEDICAL COMPONENTS TO THE LUNGS

TECHNICAL FIELD OF THE INVENTION

The present invention relates generally to pharmaceutical formulations. Particularly, the present invention relates to a new delivery system for delivery of medical components to the lungs, with high drug loading and its utility in the fields of pharmaceutical formulation, drug delivery, medicine and diagnosis.

BACKGROUND

The lungs are located in the chest and are constructed as a tube system that divide over 20 times and ends up in the lung tissue. Lung tissue is constructed as a system of sacs (alveoli) filled with air. The alveoli are surrounded by capillaries. When a person inhales, oxygen moves from the alveoli to the surrounding capillaries and into the bloodstream. At the same time, carbon dioxide moves from the bloodstream to the capillaries and into the alveoli. Thus, the lungs function in the respiratory system is to extract oxygen from the atmosphere and transfer it into the bloodstream, and to release carbon dioxide from the bloodstream into the atmosphere, in a process of gas exchange. The lungs are part of a complex apparatus, expanding and relaxing thousands of times each day. The central airways are stabilized by cartilage tissue and the more distal airways contain smooth muscles and elastic tissue.

Lung diseases are some of the most common medical conditions in the world. Diseases localized to the lungs may be both disabling and deadly and can benefit from getting the drug delivered directly to the lung. Smoking, infections and genetics are responsible for most lung diseases. Lung disease can result from problems in any part of the respiratory system.

There are three main types of lung diseases; 1) airway diseases affecting the tubes (bronchi), 2) lung tissue diseases affecting the structure of the lung tissue and 3) lung circulation diseases affecting the blood vessels in the lungs.

The most common lung diseases include acute inflammations such as bronchitis (in the airways) and pneumonia (lung tissue), chronic inflammations such as asthma (in the airways) and fibrotic lung disease (lung tissue), chronic obstructive pulmonary disease (COPD), emphysema, pulmonary edema, pneumothorax, pulmonary embolus and lung cancer.

Lung cancer is the most lethal type of cancer and accounted for approximately 1.59 million deaths worldwide in 2012. In Norway, about 20% of deaths related to cancer is caused by lung cancer. Most primary lung cancers are carcinomas, mainly located in the airways, and the two main types are small-cell lung carcinoma (SCLC) and non-small-cell lung carcinoma (NSCLC). Whereas SCLC is known to respond to chemotherapy and radiotherapy, the standard treatments for NSCLC include surgery, chemotherapy, radiation, laser and photodynamic therapy. The success rates of the various treatments are depending on type of cancer, the stage (degree of spread), and the person's overall health. Although improved in recent years, the prognosis for lung cancer patients is still poor.

Chemotherapy can be defined as the treatment of cancer with one or more cytotoxic anti-neoplastic drugs (chemotherapeutic agents) as part of a standardized regimen. The term encompasses a variety of drugs, which are divided into broad categories such as alkylating agents and antimetabolites. Traditional chemotherapeutic agents act by killing cells that divide rapidly, a critical property of most cancer cells. This is achieved by impairing mitosis (cell division) or DNA synthesis.

Chemotherapeutic agents are most often delivered parenterally. With traditional parenteral chemotherapy, typically only 0.001-0.01% of the injected dose reaches the tumor. Many current chemotherapy drugs unfortunately have excessive toxicity to healthy tissues and a limited ability to prevent metastases. As traditional chemotherapy does not have high enough efficacy compared to the severe side effects, the dosages is often limited to the sub-optimal making treatment of tumors in the lungs very difficult.

The use of nanotechnology in medicine offers many possibilities. Two areas in which the use of nanotechnology has begun to demonstrate particular value are drug delivery and molecular imaging. Nanoparticles (NPs) for delivery of medical components have the potential to circumvent many challenges associated with traditional delivery approaches, including adverse side effects and poor efficacy due to non-specific bio distribution. As such, NPs as carriers for anti-cancer drugs are shown to offer great potential. However, since uptake of NPs in tumors is often insufficient and the distribution is heterogeneous, systems to enhance the delivery of NPs is of great interest. As demonstrated by Afadzi et al.(1) and Eggen et al.(2) ultrasound is shown to enhance the delivery of NPs to solid tumors. It has also been proposed that commercially available microbubbles (MBs) may be utilized with ultrasound to enhance uptake of drug in tissues. Even further, Eggen et al.(3) (J Control Release. 2014 Aug. 10; 187: 39-49. doi: 10.1016) has proposed the use of ultrasound in connection with NP stabilizing MBs. However, all this prior art utilizes ultrasound to enhance the uptake of the medical component and ultrasound has limited effect in lung tissue due to ultrasound being reflected in the air-tissue interface and thereby have very limited tissue penetration in the lungs.

In U.S. Pat. No. 9,421,194B2, it is disclosed a lung targeting dual drug delivery system comprising a gel microparticle and nanoparticles. This system depends on intravenous administration of particles of a particular size to be trapped in the capillary beds of the lungs. Another system is described in Xu et al(4), which describes a discoidal micrometer-sized particle that can be loaded with chemotherapeutics.

There is a still need for alternate and flexible delivery systems specifically targeting lungs to enhance the amount of drug to reach its target pathology in lung tissue, alleviating disadvantages found in the prior art. Preferably, such delivery systems will also limit the toxicity towards healthy tissue.

SUMMARY OF THE INVENTION

The present inventors have surprisingly found that delivery of medical components to lungs and lung tissue can be achieved using a delivery system comprising gas-filled microbubbles (MBs), a plurality of nanoparticles (NPs) and at least one medical component associated with one or more of the NPs.

The delivery system does not use ultrasound to aid release and uptake of NPs in target tissue.

The present invention provides a delivery system, a method of preparing a delivery system, use of the delivery system in medicine and composition comprising the delivery system.

Specifically, the present invention provides the following aspects:

In a first aspect, the invention provides a delivery system for use in medicine comprising a gas-filled microbubble, a plurality of NPs, wherein at least one of the NPs is loaded with at least one medical component, for delivery of the medical component to a target tissue being a lung, a tissue of a respiratory system and/or a nearby tissue, such as tissue in proximity to the respiratory system, such as a cartilage tissue, a smooth muscle tissue and/or an elastic tissue in proximity to the airways.

In a preferred embodiment, the delivery of the nanoparticles and the medical component to the target tissue is without using ultrasound, such as focused ultrasound.

In one embodiment, the medical use is for diagnosis or treatment of lung disease.

In one embodiment, the plurality of nanoparticles is associated with the gas-filled microbubble, such as surface-associated. As described herein, the plurality of nanoparticles associated with the gas-filled microbubbles may stabilize the microbubbles.

In another embodiment, the delivery system may further comprise at least one free nanoparticle and at least one medical component associated with the at least one free nanoparticle.

In a further embodiment of the invention, at least one of the plurality of nanoparticles are coated with polyethylene glycol (PEG).

In yet another embodiment at least one of the plurality of nanoparticles further comprise at least one targeting agent.

In one embodiment, the delivery system further comprises a pharmaceutically acceptable carrier.

Another embodiment describes a delivery system wherein the gas-filled microbubble comprises a gas selected from the group consisting of: perfluorocarbon (PFC), air, noble gases, sulfuric fluoride gases, such as sulfur hexafluoride (SF6) gas, halogens, or air-components, such as nitrogen (N2), oxygen (O2), argon (Ar), carbon dioxide (CO2), helium (He), neon (Ne) and methane (CH4).

In one embodiment the gas is PFC. In another embodiment the gas is air or air-components. In yet another embodiment the gas is sulfur hexafluoride (SF6) gas. In a further embodiment the gas is not PFC.

In a further embodiment, the gas-filled microbubbles further comprise a surface-active compound, such as casein or serum albumin.

In yet another embodiment, the delivery system further comprises a modifying agent. In a preferred embodiment, the modifying agent is urea.

One embodiment of the delivery system is a system as described, wherein the mean diameter of the gas-filled microbubbles associated with nanoparticles is in the range 0.5 to 30 µm.

In another embodiment of the delivery system according to the invention, the medical component is selected from the group consisting of: cytotoxic/cytostatic drugs, antibiotics, mucus-dissolving agents (mucolytics), anti-inflammatory drugs, a pulmonary therapeutic drug, respiratory agents, immunotherapeutic drugs, gene-modifying agents, chemopotentiators, diagnostic agents, contrast agents.

In a second aspect, the invention provides a delivery system comprising a gas-filled microbubble, a plurality of NPs, wherein at least one of the NPs is loaded with at least one medical component, for delivery of the medical component to a lung and/or a nearby tissue, such as tissue in proximity to a lung, such as cartilage tissue, smooth muscle tissue and elastic tissue in proximity to the airways, and wherein the plurality of nanoparticles are free nanoparticles.

In one embodiment according to this aspect, the plurality of nanoparticles may be coated with polyethylene glycol (PEG).

In another embodiment of this aspect, at least one of the plurality of nanoparticles further comprises at least one targeting agent.

The delivery system according to this aspect may further comprise a pharmaceutically acceptable carrier.

In a further embodiment according to this aspect, the gas-filled microbubble comprises a gas selected from the group consisting of: perfluorocarbon, air, noble gases, sulfuric fluoride gases, such as sulfur hexafluoride (SF6) gas, halogens, or air-components, such as nitrogen (N2), oxygen (O2), argon (Ar), carbon dioxide (CO2), helium (He), neon (Ne) and methane (CH4).

In one embodiment the gas is PFC. In another embodiment the gas is air or air-components. In yet another embodiment the gas is sulfur hexafluoride (SF6) gas. In a further embodiment the gas is not PFC.

In yet another embodiment, the gas-filled microbubble further comprises a surface-active compound, such as casein or serum albumin.

In one particular embodiment, the gas-filled microbubble is a microbubble with nanoparticles associated on the surface.

In yet another embodiment, the delivery system further comprises a modifying agent. In a preferred embodiment, the modifying agent is urea.

In one embodiment of the invention according to this aspect, the mean diameter of the gas-filled microbubbles associated with nanoparticles is in the range 0.5 to 30 µm.

In another embodiment, the medical component is selected from the group consisting of: cytotoxic/cytostatic drugs, antibiotics, mucus-dissolving agents (mucolytics), anti-inflammatory drugs, a pulmonary therapeutic drug, respiratory agents, chemopotentiators, diagnostic agents, contrast agents.

In a third aspect, the invention provides a method for preparing a drug delivery system according to the first and the second aspect of the invention, comprising the steps of:
a. Synthesizing the nanoparticles to be loaded with the medical component.
b. Adding nanoparticles to a solution comprising a surface-active substance.
c. Adding gas to the solution
d. Mixing the solution to obtain gas-filled microbubbles.

In one embodiment according to this aspect, the solution in c) is mixed from 2 seconds to 60 minutes, preferentially 1 to 10 minutes.

In another embodiment of this aspect, the solution in c) is mixed by stirring at 500 to 50 000 rpm, preferentially 1 000 to 30 000 rpm In yet another embodiment, the surface-active substance in b) is serum, or protein or lipid or surfactant In a fourth aspect of the invention, the delivery system according to any of the first and second aspect of the invention, is for use in medicine by delivery of the medical component to a lung and/or to a respiratory system and/or a nearby tissue, such as cartilage tissue, smooth muscles and elastic tissue of the airways.

Different embodiments according to this aspect describe use of the invention for diagnosis of a lung disease or for treatment of a lung disease. In different embodiments, the lung disease is any one disease affecting the lungs or the respiratory system, such as 1) airway diseases affecting the tubes (bronchi), 2) lung tissue diseases affecting the structure of the lung tissue and 3) lung circulation diseases affecting the blood vessels in the lungs.

The lung disease may in different embodiments be acute inflammations such as bronchitis (in the airways) and pneumonia (lung tissue), chronic inflammations such as asthma (in the airways) and fibrotic lung disease (lung tissue), chronic obstructive pulmonary disease (COPD), emphysema, pulmonary edema, pneumothorax, pulmonary embolus and lung cancer.

In one embodiment, the delivery system according to the different aspects are for parental administration, such as for injections, intravenous or intra-arterial administration.

In one particular embodiment, the delivery system is for targeted delivery to the lungs.

It is also described methods of treating or diagnosing a lung disease comprising administering a delivery system according to the claims 1-20 to a patient in need thereof.

As will be understood by the skilled person, every embodiment and aspect concerning the medical use of the present invention as described herein is likewise applicable for the method for treatment or diagnosis of lung disease in a patient.

In a last aspect, a composition or solution is provided comprising the delivery system according to the first and the second aspect of the invention. The composition or solution may be a pharmaceutical formulation comprising pharmaceutically acceptable excipients and diluents.

DEFINITIONS

As used herein, the phrase "at least one" followed by a list of two or more items, such as "A, B, or C," means any individual one of A, B or C as well as any combination thereof.

The term "microbubbles (MBs)" refers to vesicles that are generally characterized by the presence of one or more shells, walls or membranes surrounding an internal void that is filled with a gas or precursor thereto. They have a diameter typically in the range from 1 to 10 μm, or more typically from 1 to 6 μm.

As used herein, the term "nanoparticles (NPs)" describe particle of any shape with dimensions in the 1 nm and 1000 nm range, typically under 800 nm, more typically under 500, 400, 300, or 200 nm. In one embodiment, the NPs as used herein is typically 70 to 200 nm. Typically, the NPs are spherical.

The term "associated with" as used herein in connection with microbubbles and nanoparticles, is meant to describe the interaction between microbubbles and nanoparticles.

The interactions may include chemical bonds caused by electrostatic force of attraction between atoms with opposite charges, or through the sharing of electrons as in the covalent bonds. The chemical bonds may be both "strong bonds" such as covalent or ionic bonds and "weak bonds" such as different van der Waals forces, Dipole-dipole interaction, the London dispersion force and/or hydrogen bonding.

The term "medical component", as used herein, is meant to include both diagnostic and therapeutic agents and theranostics, a combination of therapeutics and diagnostics. Examples of therapeutic agents for treatment of lung diseases are antibacterial agents, anti-fungi agents, beta-agonists, corticosteroids, chemoterapeutic agents, chemopotentiators etc. The term "diagnostic" or "diagnostic agent" used herein is any chemical moiety that may be used for diagnosis or imaging a patient. Examples of diagnostic agents are imaging agents such as fluorescent dyes and magnetic resonance imaging.

Targeted drug delivery is a method of delivering medication to a patient in a manner that increases the concentration of the medication in some parts of the body relative to others. As used herein, "targeted delivery" or "targeting delivery" refers to the mechanism by which a delivery system is transported to its proper destination. Passive targeting is based on the longevity of the pharmaceutical carrier in the blood and its accumulation in pathological sites with compromised vasculature. In passive targeting, the drug's success is directly related to circulation time. Active targeting is based on the attachment of specific targeting moieties to the surface of pharmaceutical carriers to recognize and bind pathological cells. Active targeting of NPs may be used in combination with passive targeting to enhance the effects of passive targeting by making the NP more specific to a target site.

As used herein, "targeting moiety(ies)" refers to any suitable moiety which targets or causes the particle to become localized at specific locations within a subject. The targeting moiety may be a moiety that contain a functional group that can be reacted with the terminus opposite to the amino group terminus of polyalkylene glycol of NPs. Suitable functional groups are those capable of forming a covalent bond with a polyalkylene glycol, such as amino, hydroxy, azide, alkyne and thio. The conjugation of a targeting moiety to a polyalkylene glycol may be performed by any method routinely used in the art, such as "click" chemistry. It should be appreciated that a single targeting moiety or a mixture of different targeting moieties may be used. Example targeting moieties are selected from the group consisting of an amino acid, protein, peptide, antibody, antibody fragment, saccharide, carbohydrate, glycan, cytokine, chemikine, nucleotide, lectin, lipid, receptor, steroid, neurotransmitter, cell surface marker, cancer antigen, glycoprotein antigen, aptamer, or mixtures thereof. Particularly preferred targeting moieties include linear and cyclic peptides.

As used herein, "target tissue" refers to a tissue or an organ on which a medical component exerts its action; generally, a tissue or an organ that will benefit from receiving the medical component. According to the invention, the target tissue is a lung, a tissue of a respiratory system and/or a nearby tissue, such as tissue in proximity to the respiratory system, such as a cartilage tissue, a smooth muscle tissue and/or an elastic tissue in proximity to the airways, all of which may be appropriately targeted by either passive and/or active targeting by the delivery system.

"Surface-active compound" and "stabilizing agent" are used interchangeably and refers to compounds such as proteins, polymers, lipids and/or surfactants. Examples of suitable surface-active compounds are polysorbate (Tween), albumin, casein and phospholipid. The surface-active compound is added to the delivery system of the invention to stabilize the gas-filled microbubbles.

As used herein, "modifying agent" refers to agents that can modify the surface of the microbubbles, to further promote a stabile association between the microbubbles and the nanoparticles. This can be achieved by modifying the interaction between the surface-active compounds and the nanoparticles. The modifying agent can form complexes or cross-links between the MBs and NPs and hence increase the stability of the delivery system.

The term "pharmaceutically acceptable" as used herein denotes that the system or composition is suitable for administration to a subject, including a human patient, to achieve the treatments described herein, without unduly deleterious side effects in light of the severity of the disease and necessity of the treatment.

As used herein, the terms "treat," "treating," and "treatment" are used synonymously to refer to any action providing a benefit to a patient at risk for or afflicted with a disease, including improvement in the condition through lessening, inhibition, suppression or elimination of at least one symptom, delay in progression of the disease, prevention, delay in or inhibition of the likelihood of the onset of the disease, etc.

DETAILED DESCRIPTION

NPs as carriers of medical components is a promising solution for treating diseases as they may provide a more local and targeted treatment. However, NPs as carriers does not come without challenges. One of the main challenges using NPs is achieving high enough concentrations of NPs at the target site. As a solution to this problem, the inventors have found that by administrating the NPs with MBs, one can achieve a much higher concentration of NPs at the target site than if NPs is administrated by itself. A plurality of NPs may be comprised in a delivery system with MBs, either along with the MBs in a solution or directly associated with the MBs. By further loading each NP with a desired medical component, the amount of medical components delivered to the target site is greatly enhanced.

Another challenge with the use of NPs as carriers is that most of free NPs in the blood stream often end up in the liver and spleen. However, the inventors have found that this may also be addressed by a delivery system comprising both NPs and MBs. Previously, a delivery system comprising NPs and MBs have been used with focused ultrasound to target specific disease sites. These MBs are developed to assure long circulation time and no organ-specified affinity, Surprisingly, the inventors have now found that a delivery system comprising NPs and gas-filled MBs creates an optimized system for targeted delivery of drugs to the lungs, due to the discovery that MBs have a tendency to accumulate in the lungs.

Accordingly, the result of this invention is an improved delivery system, where medical components for diagnosis and/or treatment of diseases related to the respiratory system is delivered to the lungs. One advantage of the invention is that it is independent of ultrasound previously used to target the delivery drugs associated with MBs.

In a first aspect, the invention is a delivery system for use in medicine comprising gas-filled MBs, a plurality of NPs and one or more medical component for targeted delivery to lungs and/or the relevant tissue of the respiratory system.

The MBs applicable in the system according to the invention may be any regular commercially available contrast microbubble, such as Albunex (GE Healthcare), Optison (GE Healthcare), Sonazoid (GE Healthcare), Sonovue (Bracco) or other regular, contrast MBs known to the skilled person. In one embodiment of the invention, the MBs comprised in the delivery system is a MB with a shell of NPs associated to the surface. Such MBs is produced in a solution of NPs, as described herein. An advantage with this embodiment is the stabilizing effect of the NPs associated on the surface of the MBs.

In one embodiment, the MBs according to the invention may be a gas-filled MB, filled with a gas or a precursor thereto. In preferred embodiments, the gas comprises perfluorocarbons or sulfuric fluoride gases or halogens or air or any gases known to be components in air, such as but not limited to nitrogen ($N_2$), oxygen ($O_2$), argon (Ar), carbon dioxide ($CO_2$), helium (He), neon (Ne) and methane ($CH_4$).

Without being bound by theory, the solubility of the gas comprised in the MBs may influence the ability of the MBs to circulate in the blood and the ability to accumulate in the respiratory system. For example, studies have demonstrated that MBs that are filled with PFC gases has an extended circulation time. This may be due to the low solubility of PFC in blood.

In one embodiment the gas is PFC. In another embodiment the gas is not PFC. In a further embodiment the gas is air, or any gas known to be components in air. In yet another embodiment the gas is a sulfuric fluoride gas, preferably sulfur hexafluoride (SF6) gas.

Commercially available MBs consist of a suspension of gaseous MBs stabilized by a shell of lipids and/or proteins and/or other surfactants. Accordingly, in one embodiment of the invention, the MBs is optionally made with the addition of a surface-active compound. The surface-active components may be such as proteins, polymers, lipids or surfactants. The function of such surface-active compound is to stabilize the microbubble. If the surface-active compound is a protein, preferred embodiments are albumin or casein. If the surface-active compound is a lipid, a preferred embodiment is a phospholipid. Optionally the MBs may also contain further stabilizing agents and excipients, such as cholesterol or polyoxyethylene-polyoxypropylene. With respect to the albumin MBs, these MBs may be derived from human or bovine serum albumin (HSA or BSA) or from other suitable biocompatible albumin sources, including synthetic or synthesized albumin.

The delivery system according to the invention comprises a plurality of NPs. The NPs applicable in the delivery system may be any NP capable of loading a medical component, such as diagnostic agents and therapeutic agents. The NPs are used as delivery vehicles, accordingly a variety of nanoparticulate systems are applicable in the system according to the invention. These include polymeric micelles, polymers, liposomes, low-density lipoproteins, solid lipid NPs, dendrimers, hydrophilic drug polymer complexes, ceramic NPs and other NPs known to the skilled person. NPs as described in Kumari et al, 2010 are applicable in a system according to the invention.

Optionally, the delivery system according to the invention can further comprise a modifying agent. The function of the modifying agent is to modify the interaction between the components of the delivery system. The modifying agent can form complexes or cross-links between the microbubbles and/or the surface-active compounds and the nanoparticles and hence increase the stability of the delivery system. In one embodiment, the modifying agent introduces interactions between the surface-active compound and the nanoparticles. In one particular embodiment, the modifying agent is urea. In one preferred embodiment, the delivery system comprises a protein, preferably casein, as a surface-active compound and urea as a modifying agent. Urea (H2N—CO—NH2) is known as a denaturant for protein. It is highly polar and therefore interferes with the hydrogen bonds involved in protein folding. The ability of urea to form hydrogen bonds is well known. This has been attributed to the positive character of the hydrogen atom covalently bonded to the strongly electron-negative nitrogen atom of the amino group of the urea molecule. Urea can also form a complex with acid groups on the NP surface and modify the hydrophilicity of the NPs.

In an embodiment of the invention, wherein the delivery system comprises a surface-active compound being a protein and a modifying agent being urea, the amount of medical compound delivered to the targeted tissue is enhanced. By introducing stronger interactions between the surface-active compounds and the NPs, urea will result in a more stable MBs. Accordingly, the function of urea is to modify the hydrophobicity and/or the hydrophilicity of the MBs and/or the NPs comprised in the delivery system. As will be understood by a person skilled in the art, different modifying agents are applicable. Without being bound by theory, it is believed that the modification of the MBs, the surface-active compound and/or the NPs will enhance the stability of the association between MBs and NPs in the delivery system. As the association between MB and NPs is enhanced, the number of NPs reaching the targeted lung tissue will be larger thereby enabling a greater amount of medical component to reach the target tissue. This has been demonstrated in Example 4 (see FIG. 7).

In one embodiment, the NPs as described herein may be polymeric NPs comprising biodegradable polymers such as poly(lactic acid), poly(glycolic acid) and poly(alkyl cyanoacrylate) (PACA). PACAs are known to the skilled person and may be as described in WO2014/191502 A1, both with and without targeting moieties.

PACAs were first introduced to the medical field as surgical glue but has been extensively studied as a material for drug delivery vehicles. PACA NPs can easily be prepared by in situ polymerization of alkyl cyanoacrylate monomers encapsulating a wide range of drugs with high loading capacity. As the monomers are hydrophobic, PACAs are especially suitable for encapsulating lipophilic drugs, thereby improving the delivery of poorly blood-soluble drugs. The flexibility of the PACA nanoparticulate system allows for good control and design of end-use properties. The size and degradation rate can be regulated, and the surface functionalized, allowing for both long circulation times and targeted delivery. In one embodiment, the process of preparing PACA NPs includes customizing the NP surface by introducing hydrophilic polymers and incorporating medical components, such as drugs and contrast agents for various imaging modalities. Accordingly, this embodiment of the delivery system constitutes a highly versatile and flexible system, allowing for delivery of different medical components to the lungs, e.g. the respiratory system and adjacent tissue.

In another embodiment of the invention, at least one of the NPs is a lipid-based NP. The lipid-based NPs applicable in the system according to the invention may be nanostructured lipid carriers (NLC), such as composed of e.g. stearic acid and isopropyl palmitate. Such lipid-based NPs offer flexibilities with regard to the lipid core (solid and liquid) as well as the stabilizing ligands. This enables tailoring to specific physico-chemical environments and drug compatibility. The particles can be covered with hydrophilic polymers making them water-dispersible and non-aggregating in buffer and biological media. Further, the particle's surface can optionally be further functionalized with targeting moieties, such as with ligands or other molecules of interest. This offers the possibility for active targeting to specific cells.

In yet another embodiment, the NPs are coated with polyethylene glycol (PEG). Coating NPs with PEG is a common approach for avoiding clearance by the immune system.

Another important feature of the NPs is the possibility to incorporate imaging agents such as fluorescent dyes and magnetic resonance imaging (MRI) or positron emission tomography/single-photon emission computed tomography (PET/SPECT) contrast agents, achieving a combination of therapeutics and diagnostics, so called 'theranostics'.

In one embodiment of the invention, the delivery system comprises gas-filled MBs and a plurality of NPs, wherein the plurality of NPs is associated with the gas-filled MBs. According to this embodiment, the plurality of NPs may be surface-associated to the MB. Optionally, the delivery system according to this embodiment further comprises free NPs, which may be or not be the same as the NPs that are surface-associated to the MBs. The NPs may be any NPs, optionally further surface functionalized, such as PEGylated and/or targeted or functionalized with any other surfactant known to the skilled person, such as mentioned in Gamucci et al.(5)

Without being bound by theory, the association between the NPs and MBs may be the result of the formation of so-called Pickering emulsions. It is known that solid particles with intermediate hydrophobicity can adsorb strongly at the interface between immiscible fluids such as oil-water, enabling the formation of Pickering emulsions, i.e. emulsions stabilized by solid particles of nano- or micrometer size. In the same manner, solid particles can be used to stabilize gas-water interfaces. However, few materials inherently possess the sufficient balance of hydrophobicity and hydrophilicity essential for particle-stabilizing action. According to such embodiment, the delivery system of the invention comprises NPs that can be used to stabilize the gas-water interface by self-assembly at the MB surface. The result is very stable MBs. Such NP-stabilized MBs are shown to have long shelf life.

In one particular embodiment, the NPs are polymeric NPs, such as PACA NPs, which may be used to stabilize MBs by self-assembly onto the MB surface. This will result in MBs with a particular stabilizing shell of NPs. The mean diameter of the gas-filled MBs associated with NPs is in the range from 0.5 to 30 μm, such as from 1-10 μm.

In another embodiment of the invention, the plurality of NPs comprised in the delivery system is free NPs. An observed advantage of the delivery system according to the invention is the enhanced concentrations of drugs that may be delivered to the target site. This may be contributed to the number of drug-filled NPs associated on the surface of the MBs. However, upon injection into the blood, an additional number of free NPs will also follow the MBs to the target site in the lungs. Accordingly, one embodiment of the invention is a delivery system comprising a gas-filled MB, a plurality of NPs and at least one medical component associated with one or more of the NP for delivery to the lungs, wherein the plurality of NPs are free NPs. The NPs may be any NP, optionally further surface functionalized, such as PEGylated and/or targeted. The delivery system according to this embodiment may further comprise a pharmaceutical acceptable carrier. The gas-filled MB according to this embodiment may be any MBs, such as commercially available gas-filled MBs known to the skilled person, or a gas-filled MB further stabilized by a shell of NPs on the surface. The plurality of free NPs may or may not be the same NPs as the ones stabilizing the surface of the MBs. Accordingly, the delivery system may comprise several different NPs, either surface-associated to the gas-filled MBs and/or comprised as free NPs. In one particular embodiment, the delivery system of the invention comprises gas-filled MBs with a plurality of NPs associated to the surface and a further plurality of free NPs. The additional free NPs contribute to a further enhanced concentration of medical component reaching the target site. According to this embodiment of the invention the increased concentration of medical component may be attributed to the high numbers of NPs associated on the surface of the MBs, as well as the additional free NPs, which will follow the gas-filled MBs to the lungs.

The medical component comprised in the delivery system of the invention may be selected from the group consisting of: cytotoxic/cytostatic drugs, antibiotics, mucus-dissolving agents (mucolytics), anti-inflammatory drugs, a pulmonary therapeutic drug, respiratory agents, immunotherapeutic drugs, gene-modifying agents, chemo potentiators, and diagnostic agents, such as contrast agents. In one particular embodiment, the medical component is cabazitaxel.

As demonstrated in the Examples, the gas-filled MBs and the plurality of NPs accumulates in lungs. Accordingly, the delivery system function as a highly passively targeting delivery system for delivery of medical components to the target tissue in the respiratory system and/or the nearby tissue. The NPs may be further actively targeted to specific diseases in the target tissue. This may be achieved by incorporation targeting moieties in the NPs. Such a delivery system will for example enable enhanced uptake of the NPs by specific pathogens causing disease in the lungs and the respiratory system, as well as by specific disease tissue, such as for example cancerous tissue with particular receptors.

Another aspect of the invention is a method for preparing a delivery system as described. In one embodiment, the method comprises the step of:
a. Adding prefabricated MBs and prefabricated NPs loaded with medical component to a solution,
b. Mixing the solution,
In another embodiment, the method comprises the step of:
a. Synthesizing NPs, loaded with a medical component.
b. Adding the NPs to a solution comprising a surface-active substance.
c. Adding gas to the solution,
d. Mixing the solution to obtain gas-filled MBs.

As described herein, the NPs in step a) may be any NP known to the skilled person suitable to be loaded with a medical component. NPs as described in Kumari et al.(6) may be synthesized as described and used in the method according to the invention.

In one embodiment, the method comprises mixing of the solution by stirring it from 2 seconds to 60 minutes. In a preferred embodiment, the solution is stirred from 1-10 minutes. Different methods for mixing the solution known to the skilled person may be utilized, such as ultrasonication, mechanical stirring, microfluidics, shaking etc.

The method of obtaining NPs associated MBs is described herein (se example 1). The method as described is simple, cheap, requires no organic solvents and is feasible to scale up. In one embodiment, NPs associated with MBs is obtained by adding gas to a solution comprising PACA NPs and mixing it to obtain gas-filled MBs. In contrast to other delivery systems, a platform based on MBs and PACA NPs, which is optimized using a one-step synthesis, allows all functionalities to be introduced in a controlled and straightforward manner.

The delivery system may be used both to diagnose lung disease and in therapy. The advantage of the system is that it specifically targets lungs and nearby tissue.

The invention is based on the discovery that when the gas-filled MBs and NPs are administrated into the bloodstream, they accumulate in the lungs. Thus, the delivery system passively targets lungs and tissue in proximity with the lungs. Accordingly, the delivery system as described is for administration into the bloodstream, such as parental administration by injection, intravenous or intra-arterial administration.

In one embodiment, the drug delivery system of the invention is for use in medicine by administration of the delivery system into the bloodstream and targeted delivery of the medical component to a lung and/or to a respiratory system and/or cartilage tissue, smooth muscles and elastic tissue of the airways, without applying ultrasound.

In previous studies, it has been demonstrated that ultrasound is necessary to aid the delivery of sufficient medical component to a target tissue, such as solid breast tumors, in order to achieve a therapeutic effect (Snipstad et al 2017). The proposed mechanism is that focused ultrasound (FUS) will create inertial cavitation, causing the microbubbles to collapse. This leads to the formation of shock waves and jet streams in the vasculature, which can create both temporary and permanent pores in the capillary wall and in cell membranes, thus allowing the drug-filled NPs to be distributed in tumors.

However, due to ultrasound being reflected in the air-tissue interface, the forces that are created by ultrasound will have very limited tissue penetration in the lungs. Accordingly, application of FUS will not be able to cause the microbubbles to collapse in lung tissue. The limitations of sonoporation and impaired ability of US waves to penetrate in lungs due to the influence of air within the lungs, has thus limited the applicability of MB-NP delivery systems in lung tissue.

In contrast to this assumption, the inventors have discovered that delivery of drug-filled NPs to lungs and tissue of the respiratory system is possible by administration of the delivery system of the invention, without applying ultrasound. Without being bound by theory, it is hypothesized that this is due to the combination of gas-filled MBs and NPs in the proposed drug delivery system, and the ability of the MBs to accumulate in the tissue of the respiratory system as a form of passive targeting. As will be obvious to the skilled person, the delivery system as described in the present application may be comprised in a composition further comprising pharmaceutically acceptable excipients and diluents. Such pharmaceutical compositions can be suitable for administration to a subject.

"Administering" when used in conjunction with a therapeutic or diagnostic means to administer a therapeutic or diagnostic systemically or locally, as directly into or onto a target tissue, or to administer a therapeutic to a patient whereby the therapeutic positively impacts the tissue to which it is targeted. "Administering" a composition may be accomplished by injection or by other methods alone or in combination with other known techniques.

Without being bound by theory, the hypothesis is that the delivery of the medical component is enhanced by several factors. One factor is the size of the delivery system; the size enables entrapment of the system in the capillary beds of the alveoli, thus making delivery of medical components to lung tissue particularly effective. Another factor is the incorporation of gas in the MBs, which are believed to influence the accumulation in the lungs. As such, the MBs with the associated NPs are not disease-targeted but can provide a benefit for different diseases and be a generic delivery system for diagnostic and therapeutic agents to lungs and the nearby tissue. In one embodiment of the drug delivery system as described herein, the medical component filled NPs are associated with the MBs, such as associated on the surface of the microbubble. In another embodiment, the drug delivery system also comprises NPs that are non-associated with the MBs, e.g. the system additionally comprises free NPs. These free NPs may also be filled with medical components. As such, they may further enhance the drug-load and hence the capacity of the drug delivery system.

As described herein, the delivery system of the invention is for use in medicine, specifically for treatment or diagnosis of diseases in the lungs, the respiratory system or in tissue in close proximity to the lungs. Such tissue can include cartilage tissue, smooth muscle tissue and elastic tissue in proximity to the airways.

Examples of diseases may be lung diseases associated with inflammation, such as cystic fibrosis and chronic obstructive pulmonary diseases, tuberculosis and lung cancer.

The examples demonstrate large accumulations of NPs filled with a medical component in healthy lungs in mice. Such increased concentration of NPs (and thus the medical component) in the lungs can lead to significantly improved diagnosis and treatment of various lung diseases. Treatment effects has been demonstrated in a pilot animal study and demonstrate that the ability of the delivery system to reduce metastasis in lungs in a model with mice and lung cancer.

It is to be understood that the embodiment described in the examples is to be regarded only as a non-limiting example of the invention and that it may be modified in many ways within the scope of the patent claims.

EXAMPLES

Example 1

Production and Characterization of NP and NP-Associated MB

Production and Characterization of Dye-Loaded Nanoparticles:

PEG-coated and dye-loaded NPs of either polymer or lipid were prepared by the miniemulsion process as follows:

Polymeric (PACA) NPs: An oil phase consisting of 2.25 g of n-butyl cyanoacrylate (BCA monomer, Henkel Loctite, Ireland), 0.1 ml of a mixture of Miglyol 810N (co-stabilizer, inactive oil, Cremer, Germany) with added DIR (near infrared dye, Marker Gene, USA) to a concentration of 25 mg/ml was prepared by thorough mixing in a glass vial kept on ice. Then, a water phase consisting of 0.125 g of Brij L23 (PEG-stabilizer, Sigma) and 0.125 Kolliphor HS15 (PEG-initiator, Sigma) in 11.5 ml 0.1 M HCl was added to the oil phase and mixed together for 30 seconds in a glass vial placed on ice using a magnetic stirrer. The oil-in-water emulsion was immediately sonicated (Branson digital sonifier 450 CE, 60% amplitude) for 3 minutes (6×30 sec intervals with 10 sec pauses) on ice. The solution was kept on rotation (15 rpm) at room temperature overnight before adjusting the pH to 5 and the polymerization continued for additional 5 hours at room temperature while rotated (15 rpm). The dispersion was dialyzed (Spectra/Por dialysis membrane MWCO 100 000 Da) extensively against 1 mM HCl (pH 3) at room temperature to remove unreacted PEG. The dialysate was replaced 3 times. The particles were stored in the acidic solution at 4° C. protected from light.

Lipid NPs: A lipid phase consisting of 0.8 g stearic acid, 0.2 g isopropyl palmitate and 0.1 ml of a mixture of Miglyol 810N (co-stabilizer, inactive oil, Cremer, Germany) with added DIR (near infrared dye, Marker Gene, USA) was pre-heated to 80° C. until melted. A water phase consisting of 0.06 g lecithin 80H, 0.24 g Andean QDP Ultra and 20 ml distilled water was prepared and pre-heated to 90° C. The lipid and water phase were mixed and sonicated in a water bath (90° C.) for 3 minutes (Branson digital sonifier 450 CE, 60% amplitude) before cooling with water. The particles were stored at 4° C. protected from light.

Zetasizer (Dynamic light scattering, Malvern) was used to determine hydrodynamic diameter, hydrodynamic diameter distribution and zeta potential of NPs. The measurements were performed at 25° C. in 0.01M phosphate buffer pH 7. The dry weight content of the final solution (NP concentration) was determined by drying the sample at 50° overnight. Dynamic light scattering method showed an NP size of 158 and 186 nm (z-average) for PACA and lipid NPs, respectively with a slightly negative charge. The polydispersity index was 0.11 (PACA NPs) and 0.17 (lipid NPs).

Production and Characterization of Cabazitaxel-Loaded NPs:

PEG-coated and cabazitaxel-loaded poly(alkyl cyanoacrylate) NPs were prepared by the miniemulsion method as follows: An oil phase containing 1.50 g of 2-ethyl-buthyl cyanoacrylate (monomer), 0.03 g of Miglyol 812 (co-stabilizer, inactive oil, Cremer, Germany) and 0.18 g cabazitaxel (cytotoxic drug, BioChemPartner, Shanghai) was prepared by thorough mixing in a glass vial. An aqueous phase containing 0.09 g of Brij L23 (PEG-stabilizer, Sigma) and 0.09 g of Kolliphor HS15 (PEG-initiator, Sigma), dissolved in 12 ml of 0.1M HCl was prepared. An oil-in-water emulsion was prepared by mixing the oil and aqueous phase and immediately sonicating the mixture (Branson digital sonifier 450) on ice for 2 minutes (4×30 sec intervals, 60% amplitude) followed by another 3 minutes (6×30 sec intervals, 30% amplitude). After sonication, the solution was rotated at 15 rpm overnight at room temperature before adjusting the pH to 5 using 0.1M NaOH. The polymerization was continued for 5 hours at room temperature while rotated (15 rpm). The dispersion was dialyzed extensively against 1 mM HCl (pH 3) at room temperature to remove unreacted PEG (dialysis membrane, MWCO 100,000 Da). The dialysate was replaced 3 times. The particles were stored in the acidic solution at 4° C. The above-mentioned method resulted in PEGylated, drug-loaded NP dispersions with concentrations of 75 mg NP/ml after dialysis. When stored in acidic condition, the particle dispersion was stable for several months, with no aggregation observed.

Zetasizer (Dynamic light scattering, Malvern) was used to determine hydrodynamic diameter, hydrodynamic diameter distribution and zeta potential. The measurements were performed at 25° C. in 0.01M phosphate buffer pH 7. The dry weight content of the final solution (NP concentration) was determined by drying the sample at 50° overnight. To calculate the amount of encapsulated drug, drug content was extracted from the particles and the extracted amount of cabazitaxel was quantified by using LC-MS/MS method.

Dynamic light scattering method showed an NP size of 142 nm (z-average) for drug-loaded NPs with a polydispersity index of 0.18. The measured zetapotential was −1 mV. The determined drug loading efficiency was 72% and the drug payload was 10.7% (% wt cabazitaxel/wt NP).

Production and Characterization of NP-Stabilized MBs:
Gas-filled MBs associated with PACA NPs were produced as follows:

A solution containing 2 wt % casein (pH 7.4) was prepared and filtered through 0.22 μm syringe filter. The dye-loaded or cabazitaxel-loaded PEGylated NPs were mixed with the casein solution and distilled water to a final concentration of 0.5 wt % casein and 1 wt % NP, with a total volume of 4 ml. The mixture was placed in a sonication batch for 10 minutes (at ambient temperatures) before the solution was saturated with gas, either air or perfluoropropane (PFC, Apollo Scientific, UK) for approximately 10 seconds. The vial was partly sealed with parafilm. Ultraturrax (25,000 rpm) was then immediately applied for 2 minutes to produce gas-filled NP-stabilized MBs. The vial was immediately sealed under gas-filled atmosphere using septum.

The average size and concentration of the resulting NP-stabilized MBs was determined from light microscopy images using a 20× phase contrast objective and cell counter (hemocytometer). MBs were counted and the size was calculated by analyzing the images using ImageJ image analyzer.

The resulting NP-stabilized MBs had an average size of 2.3 μm and concentration of 5.62E+08 MBs/ml as measured by light microscopy and image analysis.

Fluorescence microscopy (using same type of NPs only encapsulating a fluorescent dye instead of drug) and electron microscopy (FIG. 3) was used to confirm that NPs are associated with the MBs forming a stabilizing (mono)layer. When stored at 4° C., the MBs were stable for up to several months.

Example 2

Biodistribution and Lung Accumulation of Different NP-Stabilized MB in Mice

In this study, the potential of MBs associated with NPs for specific drug delivery targeted to the lungs was evaluated in healthy mice. The results show that high local concentrations can be achieved with gas-filled MBs stabilized by NPs.

Methods

The study was designed with one animal in each group. NPs labelled with a near-infrared fluorescent dye were developed according to the procedure as described in Example 1 and used. Using a whole animal imager, these NPs can be localized inside small animals.

The animal studies were approved by the Norwegian food authority (Mattilsynet). All experiments were terminal in the sense that the animals were given anaesthesia, used for experiments and sacrificed before waking up. During storage at the animal facility, the animal welfare was monitored by the engineers at the animal facility and given food and water ad libitum.

Animal Experiments:
1. An animal was randomly selected, weighted and given a subcutaneous injection of fentanyl/medetomidine/midazolam/water (2:1:2:5) which provides full anaesthesia within minutes and lasts for 2-3 hours.

2. A tail-vein catheter was placed, allowing for intravenous injections.

3. 100 ul of the desired bubbles (approx. 10e8 bubbles/ml) were injected as a bolus (injection time ~5 seconds).

4. The animals were left to sleep for the desired time before being killed by cervical dislocation.

5. Lungs, liver, kidney and spleen was then harvested in placed side by side (see result section) on the lid of a petri dish.

6. Fluorescence from the organs was imaged using a completely animal imager (Pearl).

Results
Nanoparticles:

In order to perform the animal experiments, near-infrared labelled NPs were needed. Physical characteristics of the NPs used further for producing MBs are shown in table 1.

TABLE 1

NP characteristics of the two NP batches used in animal studies

| Material | Size (z-average) | PDI | Zeta-potential | Load |
|---|---|---|---|---|
| Lipid | 186 nm | 0.17 | | DiR |
| Polymer (PACA) | 158 nm | 0.11 | −3.4 | DiR |

Figure 1:
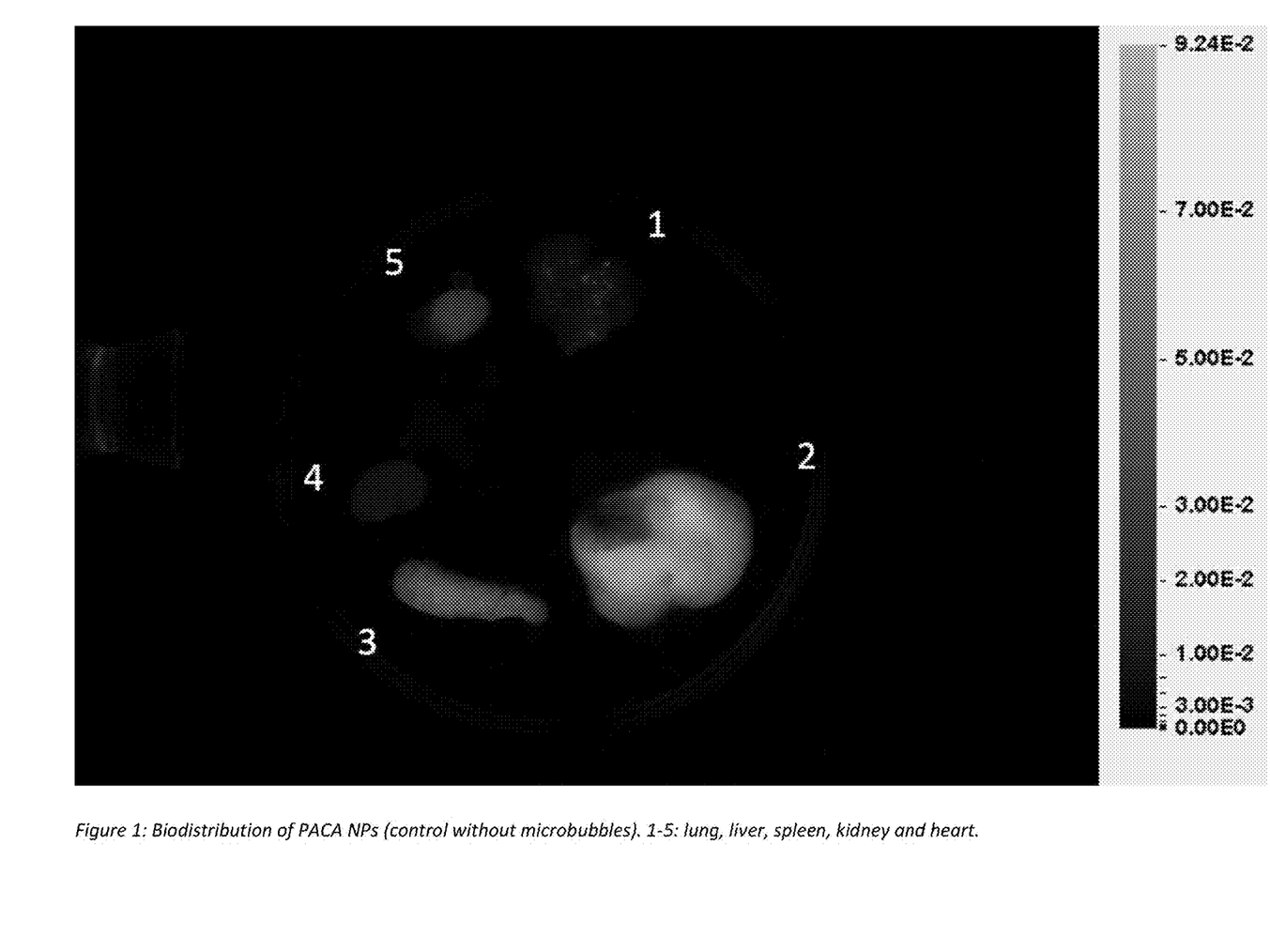
FIG. 1: Biodistribution of PACA NPs (control without MBs). 1-5: lung, liver, spleen, kidney and heart.

Microbubbles with PACA NPs:

In FIG. 1, the fluorescence from organs accumulating NPs is shown after injection of 100 ul PACA NPs (without MBs). Spotted accumulation in the lung can be observed, but the concentration is low compared to liver and spleen.

Figure 2:
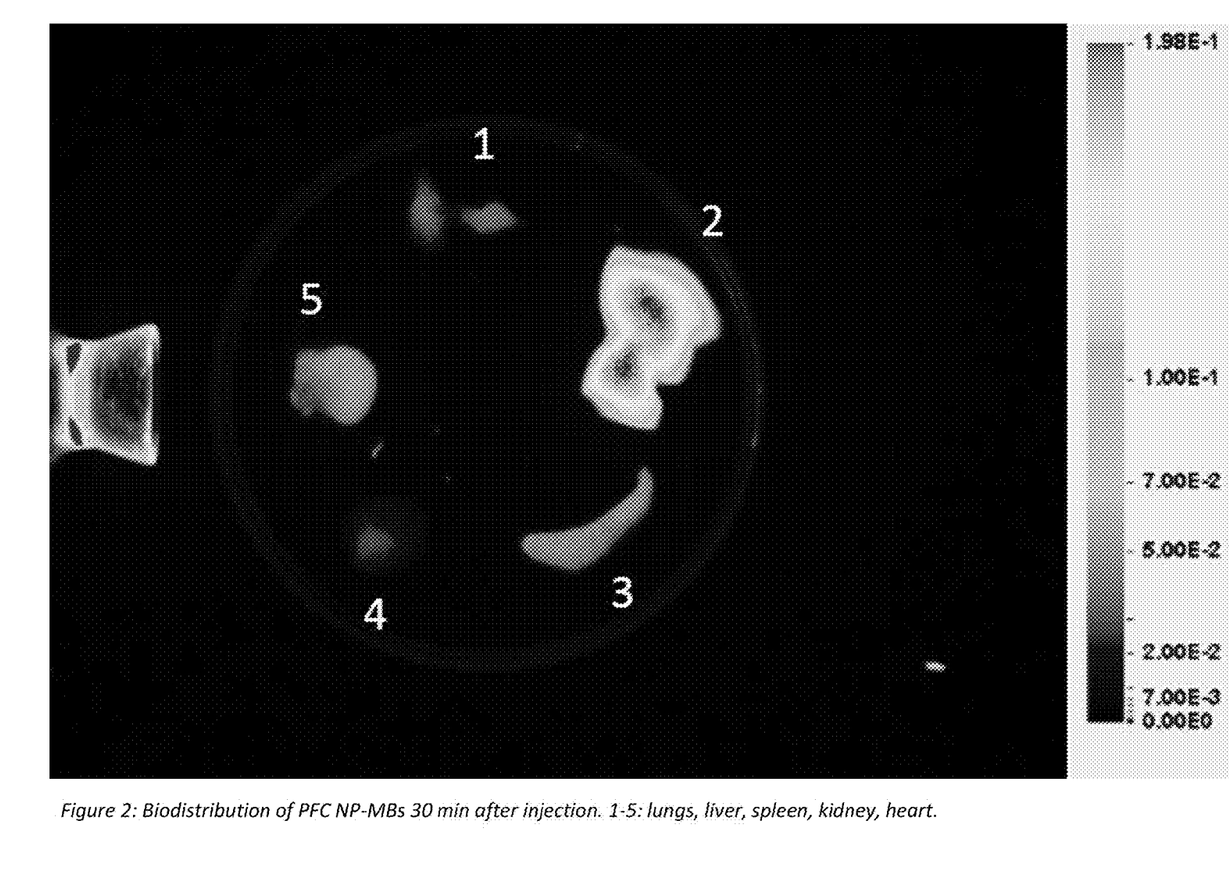
FIG. 2: Biodistribution of PFC NP-MBs 30 min after injection. 1-5: lungs, liver, spleen, kidney, heart.

Following the control containing only NPs, the delivery system comprising NP (PACA) associated with MB system was tested, wherein the MBs contained PFC gas (FIG. 2).

As can be observed in FIG. 2, small amounts of the NP-MBs accumulated in the lungs, and this was repeated in multiple animals with similar results.

Figure 3:
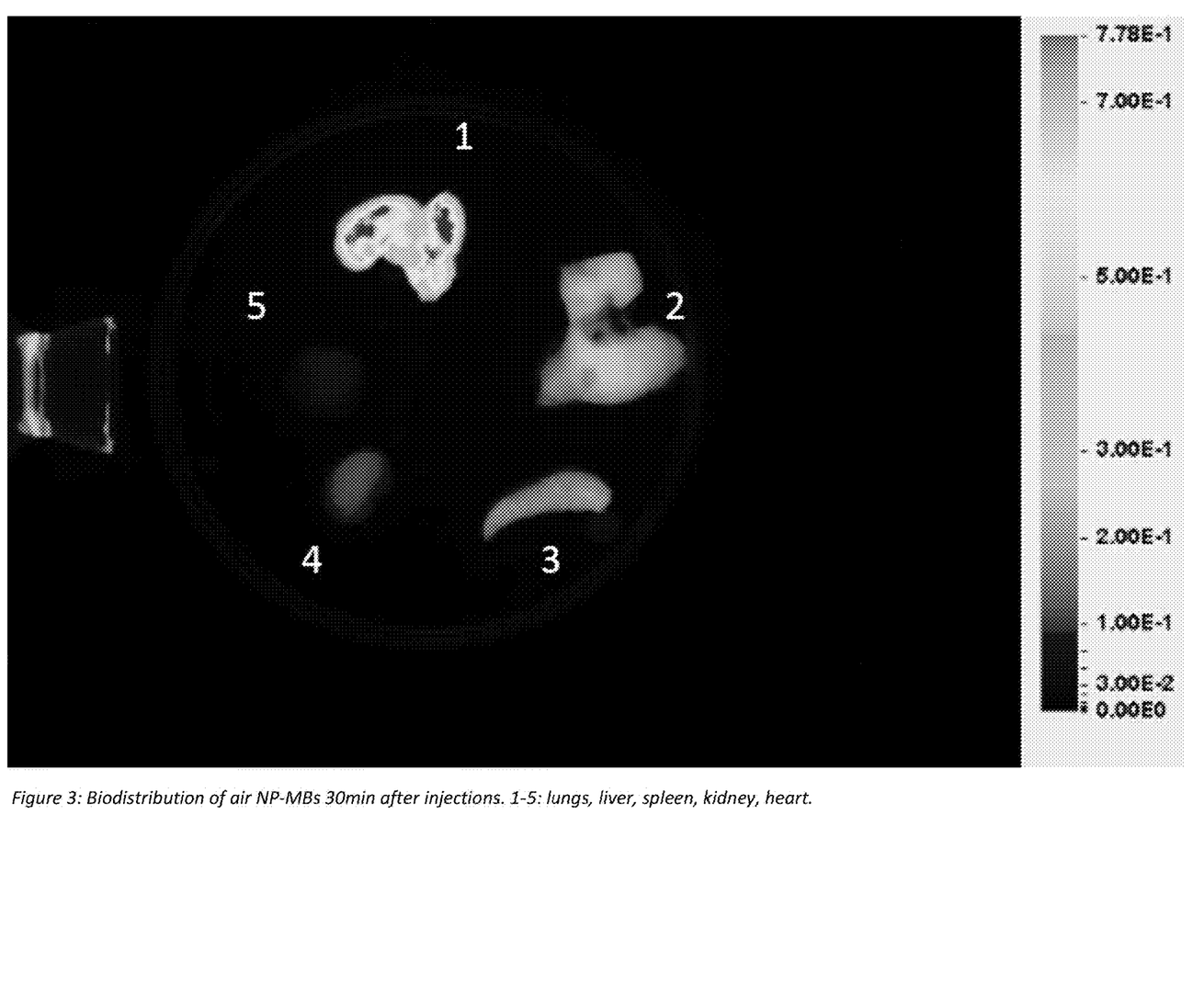
FIG. 3: Biodistribution of air NP-MBs 30 min after injections. 1-5: lungs, liver, spleen, kidney, heart.

It has previously been observed that bubbles with PFC have significantly longer circulation half-life than MBs with air, accordingly the inventors wanted to test NP-MBs filled with air next. The biodistribution of the air NP-MBs is shown in FIG. 3 and demonstrate that a larger number of DiR-loaded NPs accumulated in the lungs.

Figure 4:
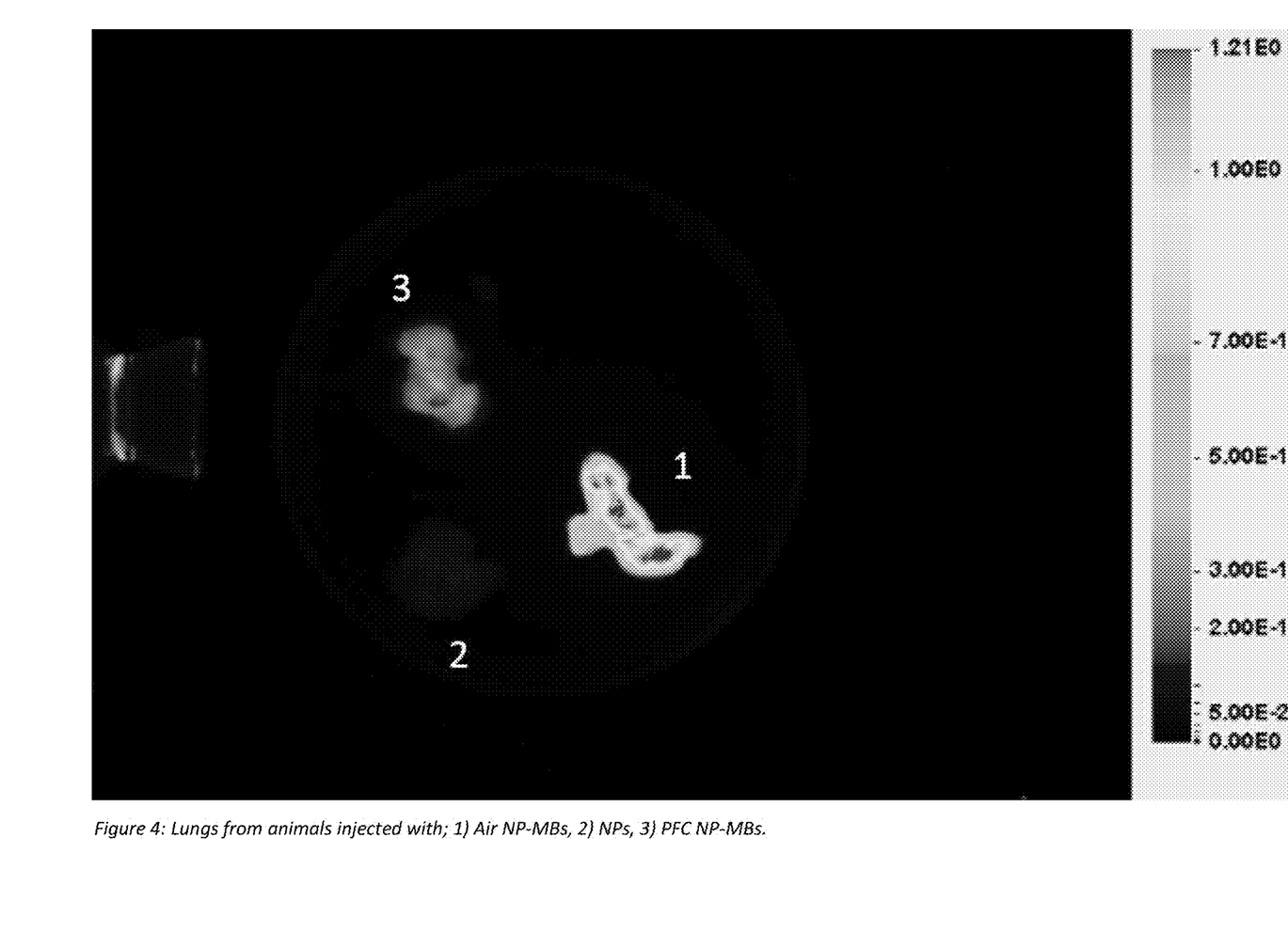
FIG. 4: Lungs from animals injected with; 1) Air NP-MBs, 2) NPs, 3) PFC NP-MBs.

In order to compare the results directly, the lungs from the three animals were placed on the same petri-dish and imaged (FIG. 4). As can be seen from FIG. 4, the lungs from mice injected with PFC NP-MBs (3) contained more DiR than the lungs from mice injected with NPs alone without MBs (2). Further, the lungs from mice injected with air NPs-MBs (1) accumulated a large number of DiR-loaded NPs.

Figure 5:
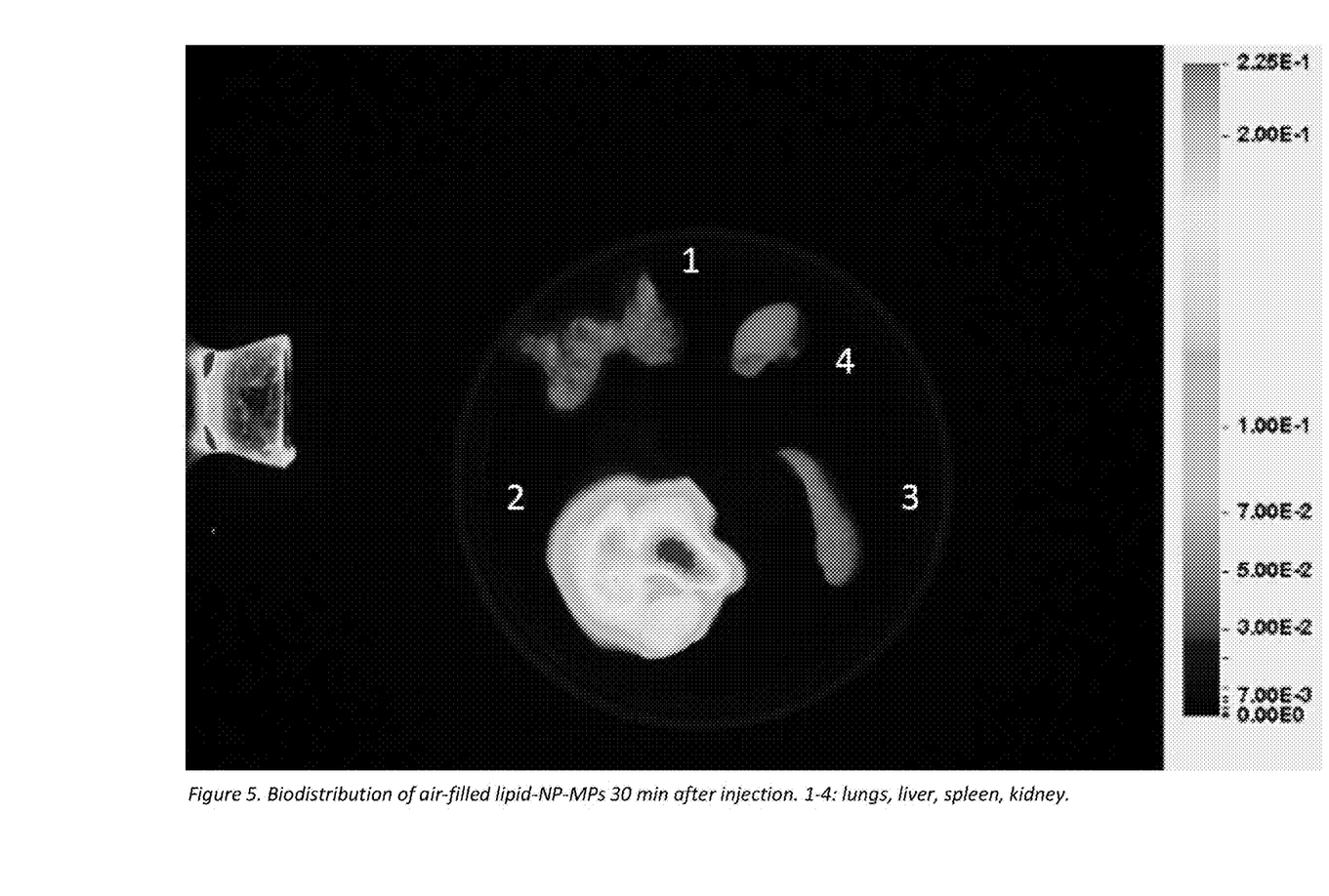
FIG. 5. Biodistribution of air-filled lipid-NP-MPs 30 min after injection. 1-4: lungs, liver, spleen, kidney.

MBs with Lipid NPs:

MBs were also produced with lipid NPs and tested with resulting biodistribution shown in FIG. 5. As can be see, also these lungs contained DiR-loaded NPs.

Figure 6:
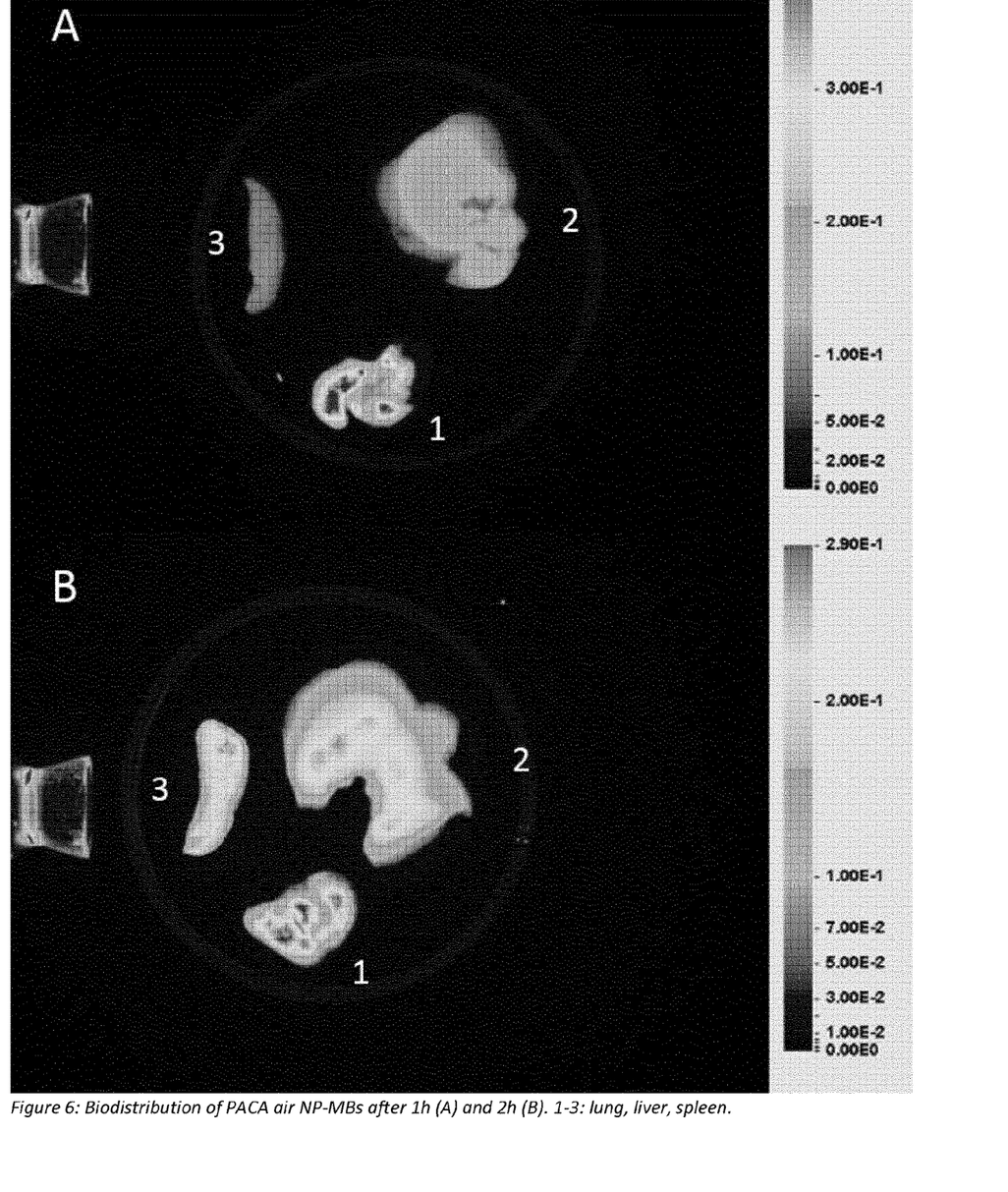
FIG. 6: Biodistribution of PACA air NP-MBs after 1 h (A) and 2 h (B). 1-3: lung, liver, spleen.

The stability of the lung accumulation was finally tested, i.e. if NPs would stay in the lungs over time or redistribute to other organs. Because the application to the Norwegian Food Safety Authority for permission to conduct animal experiments (the FOTS application) only described acute experiments, the longest time-point allowed to perform was 2 hours. The biodistribution in two animals 1 hr (FIG. 6A) and 2 hrs (FIG. 6B) after injection was examined. From the figures, there is some indication that there is a slight redistribution of NP-MBs with time, but this may be due to variation between individuals both from biology, but also from handling and sample quality, as must be expected. However, 2 hrs after injection the lungs are still the organ that have accumulated most NPs.

Conclusion

As can be seen from the comparison in FIG. 4, the injection of gas-filled MB (both PFC and air) with PACA NPs resulted in an improved accumulation of NPs in lungs compared with injection of NPs alone. In particular, the results show that the NP-MB platform consisting of PACA NPs and air MBs accumulates to very large extent in the lungs of healthy mice and that this effect gives high local concentration for at least 2 hrs (FIG. 6). FIG. 5 reveals that also air-filled MB with lipid-NP accumulates to some degree in lungs.

A high local concentration of NPs in the lungs may have a huge potential as a drug delivery system for treating lung diseases, such as for example lung cancer and respiratory disorders.

Example 3

Antitumor Activity (Treatment) Study in Mice

A pilot treatment study was preformed to investigate the potential of the delivery system in treatment of lung cancer.
Methods
Animals:
Female C57BL/6J (C57Bl/6JRj) mice were used. Animals were maintained in SPF health status according to the FELASA guidelines. Animal housing and experimental procedures were realized according to the European Regulations and NRC Guide for the Care and Use of Laboratory Animals. Animal facility was authorized by the French authorities (Agreement Np B 21 231 011 EA). All procedures using animals were submitted to the Animal Care and Use Committee of Oncodesign (Oncomet) agreed by French authorities (CNREEA agreement No 91).
Induction of B16-F10 tumors in animals:
$10^5$ B16-F10 tumor cells in 200 μL of RPMI 1640 medium were injected by the IV route into the caudal vein of mice. The day of tumor cells injection was considered as day 0 (D0).
Treatment Study:
The treatment was started at day 2 (D2). Group 1 (G1, control) received three IV injections of saline every 2 days. Group 2 (G2) received two IV injections of air-willed NP-stabilized MBs containing cabazitaxel (prepared as described in Example 1) at 10 mg cabazitaxel/kg every 2 days.

All mice were terminated at day fourteen (D14). Immediately after euthanasia, lungs were collected and weighed. The level of lung invasion was macroscopically evaluated by counting the number of metastases.
Results As can be seen from the result listed in table 2, the control group experienced more metastasis invasion. The lungs in this group were completely covered by metastasis, and the number were too large to be counted. In comparison, the mice treated with the cabazitaxel loaded NP-MBs had a percentage metastasis invasion of 20 and 30%, and metastasis count of 86 and 112, respectively.

TABLE 2

| | Mice ID | Lungs weight (g) | % invasion metastasis | Metastasis count | Observations |
|---|---|---|---|---|---|
| G1 NaCl 0.9% | 54922 | 0.153 | 40 % | Not countable (indivisible metastasis) | Nothing to report |
| | 54779 | 0.157 | 45 % | Not countable (indivisible metastasis) | Nothing to report |
| | 54600 | 0.163 | 60 % | Not countable (indivisible metastasis) | 18 mestastasis on mesentere and in a blood vessel on the pancreas, 2 masse on ovaries (left 3.67 × 7.95 mm and right 6.83 × 8.71 mm) |
| | 57188 | 0.248 | 60% | Not countable (indivisible metastasis) | Nothing to report |
| G2 NP-MBs 10 mg cabazitaxel/ kg IV | 21393 | 0.176 | 20% | 86 | |
| | 54642 | 0.198 | 30% | 112 | |

Conclusion

This was a pilot study with only limited amounts of animals. However, the results show a clear tendency between the two groups of animals, with fewer metastasis and % metastasis invasion in the group treated with the drug delivery system according to the invention compared with control, demonstrating the ability of the invention to decrease the metastasis of lung cancer in mice.

Example 4

Lung Accumulation of Different NP-Stabilized MB in Mice

In this study, the potential of different gas-filled MBs stabilized by NPs for specific drug delivery targeted to the lungs was further evaluated in healthy mice. The results show that high local concentrations can be achieved with gas-filled MBs stabilized by NPs.
Methods The study was designed with one animal in each group. NPs labelled with a near-infrared fluorescent dye were developed according to the procedure as described in Example 1 and used. Using a whole animal imager, these NPs can be localized inside small animals.

The animal studies were approved by the Norwegian food authority (Mattilsynet). All experiments were terminal in the sense that the animals were given anaesthesia, used for experiments and sacrificed before waking up.
Production of NP-Stabilized MBs:

Gas-filled MBs associated with PACA NPs were produced as follows:

A solution containing 2 wt % casein (pH 7.4) was prepared and filtered through 0.22 μm syringe filter. The dye-loaded PEGylated NPs were mixed with the casein solution and distilled water to a final concentration of 0.5 wt % casein and 1 wt % NP, with a total volume of 4 ml. The mixture was placed in a sonication batch for 10 minutes (at ambient temperatures) before the solution was saturated with gas, either SF6 or perfluoropropane (PFC, Apollo Scientific, UK) for approximately 10 seconds. The vial was partly sealed with parafilm. Ultraturrax (25,000 rpm) was then immediately applied for 2 minutes to produce gas-filled NP-stabilized MBs. In one batch, urea was added as a modifying agent in order to further promote association between microbubbles and nanoparticles. In this case, urea (2% w/v, pH 5) was added dropwise to the solution during Ultraturrax to a final concentration of 0.5% w/v urea. The vial was immediately sealed under gas-filled atmosphere using septum.

The animal experiment was performed as described in Example 2, each animal was intravenously injected with either:
A) PFC-filled MB stabilized by PEBCA NP (PFC-MBNP, GB-505, BC-26 w/PFC).
B) PFC-filled MB with urea stabilized by PEBCA NP (PFC-urea-MBNP, GB-507, BC26 w/urea, PFC).
C) SF6-filled MB stabilized by PEBCA NP (GB-509 (SF6-MBNP, BC-26 w/SF6).

Concentration of NPs in all the batches amounted to 1.17%.

Results:
The results of the accumulation of model-drug (DiR) in lungs of the animals can be seen in FIG. 7. The images are taken 30 min after the injections, and fluorescence intensities demonstrate biodistribution of drug-filled NPs in the lungs of all animals.

Figure 7:
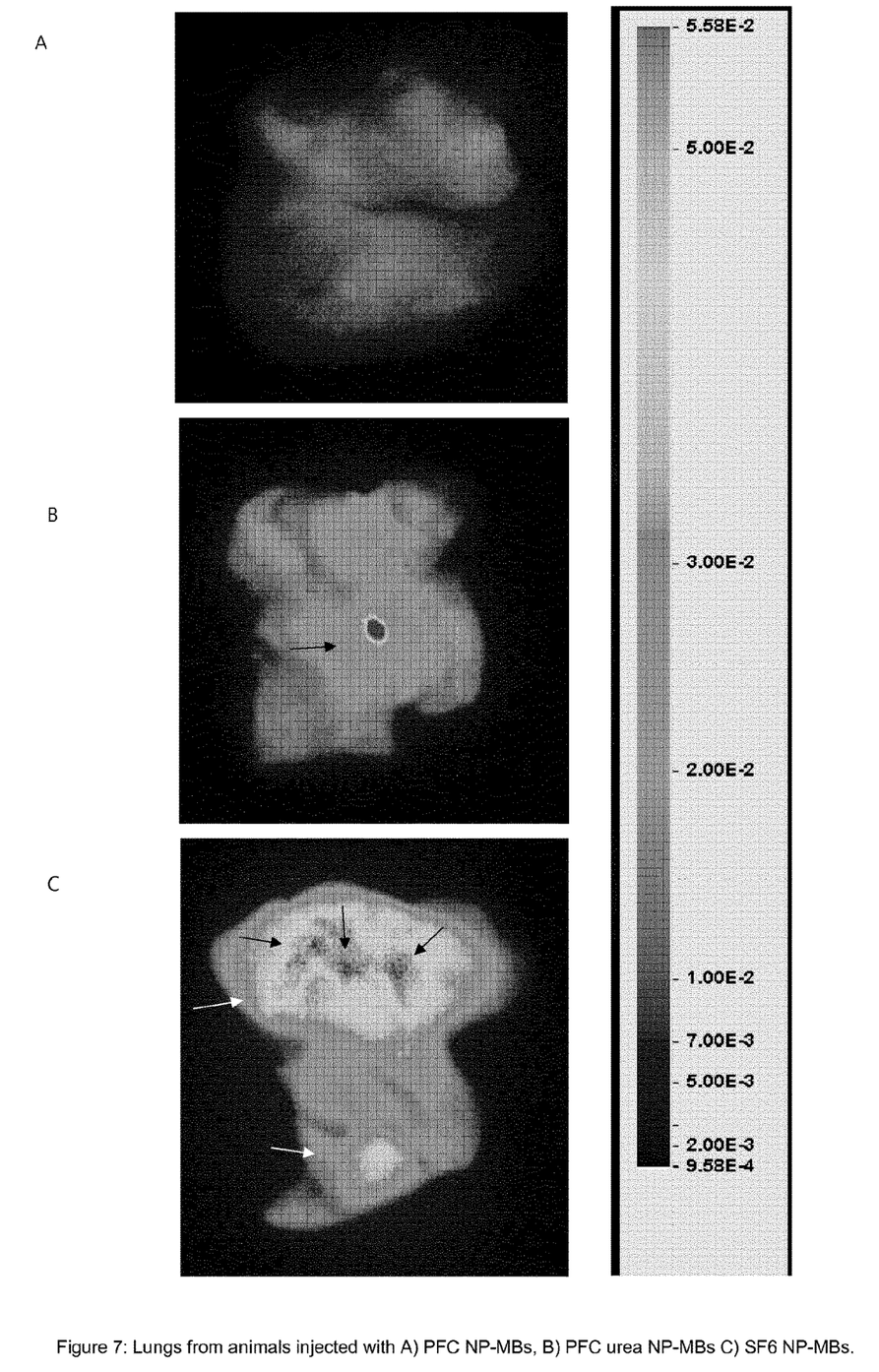
FIG. 7: Lungs from animals injected with A) PFC NP-MBs, B) PFC urea NP-MBs C) SF6 NP-MBs.

FIG. 7A shows the lungs from the animal injected with ordinary PFC-MBNP. Fluorescence intensity in the lungs demonstrate that PFC-MBNPs has accumulated and uptake of NPs with model drug.

FIG. 7B shows the lungs from the animal injected with PFC-urea-MBNP. Compared to FIG. 7A, fluorescence intensity demonstrates that urea as a modifying agent has a positive effect on NP uptake in lungs. The darker spot in the middle demonstrate the highest fluorescence intensity (above 5.58E-2, the darker spots correspond to red spots on original photos).

FIG. 7C shows the lungs from the animal injected with SF6-MBNP. Compared to both FIGS. 7A and 7B, fluorescence intensity demonstrate that accumulation of drugs is even greater in lungs of the animal injected with SF6 MBNPs. The lighter areas to the left and right (white arrows) in the pictures correspond to a fluorescence intensity between 3.00E-2 and 5.00E-2 (yellow in original pictures), while the darker spots (black arrows) in the right part demonstrate the highest fluorescence intensity (above 5.58E-2=red spots in original pictures).

Conclusion
The results demonstrate that the injection of gas-filled MB (both PFC and SF6) with PACA NPs resulted in an accumulation of NPs in lungs of healthy mice. Addition of modifying agents such as urea, which improves the association between MBs and NPs, can influence the degree of NP uptake in the target tissue.

REFERENCES

1. Afadzi M, Davies C D, Hansen Y H, Johansen T, Standal O K, Hansen R, Masoy S E, Nilssen E A, Angelsen B. Effect of Ultrasound Parameters on the Release of Liposomal Calcein. Ultrasound Med Biol. 2012; 38:476-86.
2. Eggen S, Afadzi M, Nilssen E A, Haugstad S B, Angelsen B, Davies C D. Ultrasound Improves the Uptake and Distribution of Liposomal Doxorubicin in Prostate Cancer Xenografts. Ultrasound Med Biol. 2013; 39:1255-66.
3. Eggen S, Fagerland S M, Morch Y, Hansen R, Sovik K, Berg S, Furu H, Bohn A D, Lilledahl M B, Angelsen A, Angelsen B, Davies C D. Ultrasound-enhanced drug delivery in prostate cancer xenografts by nanoparticles stabilizing microbubbles. J Controlled Release. 2014; 187:39-49.
4. Xu R, Zhang G, Mai J, Deng X, Segura-Ibarra V, Wu S, Shen J, Liu H, Hu Z, Chen L, Huang Y, Koay E, Huang Y, Liu J, Ensor J E, Blanco E, Liu X, Ferrari M, Shen H. An injectable nanoparticle generator enhances delivery of cancer therapeutics. Nat Biotechnol. 2016; 34:414-8.
5. Gamucci O, Bertero A, Gagliardi M, Bardi G. Biomedical Nanoparticles: Overview of Their Surface Immune-Compatibility. Coatings. 2014; 4:139-59.
6. Kumari A, Yadav S K, Yadav S C. Biodegradable polymeric nanoparticles based drug delivery systems. Colloids and Surfaces B: Biointerfaces. 2010; 75:1-18.
7. Snipstad et al. Ultrasound Improves the Delivery and Therapeutic Effect of Nanoparticle-Stabilized Microbubbles in Breast Cancer Xenografts. Ultrasound Med Biol. 2017 November; 43(11):2651-2669.

The invention claimed is:

1. A method of delivering at least one medical component associated with a nanoparticle to a target tissue that is a lung, tissue of a respiratory system and/or a nearby tissue and releasing the medical component into the target tissue, the method comprising intravenously administering a delivery system into the bloodstream, wherein the delivery system comprises a gas-filled microbubble, a plurality of nanoparticles and at least one medical component associated with one or more of the nanoparticles, wherein the one or more nanoparticles are not liposomes, wherein the medical component is a therapeutic agent and wherein the delivery to the target tissue and the release of the medical component is without ultrasound.

2. The method of claim 1, wherein the plurality of nanoparticles is associated with the gas-filled microbubble.

3. The method of claim 2, wherein the delivery system further comprises free nanoparticles and at least one medical component associated with the free nanoparticles.

4. The method of claim 1, wherein the plurality of nanoparticles is coated with polyethylene glycol (PEG).

5. The method of claim 1, wherein at least one of the plurality of nanoparticles further comprise at least one targeting agent.

6. The method of claim 1, wherein the delivery system further comprises a pharmaceutically acceptable carrier.

7. The method of claim 1, wherein the gas-filled microbubble comprises a gas selected from the group consisting of: perfluorocarbon, air, noble gases, sulfuric fluoride gases, halogens, and air-components.

8. The method of claim 1, wherein the gas-filled microbubble further comprises a surface-active compound and/or a modifying agent.

9. The method of claim 2, wherein the mean diameter of the gas-filled microbubbles associated with nanoparticles is in the range 0.5 to 30 µm.

10. The method of claim 1, wherein the medical component is selected from the group consisting of: cytotoxic/cytostatic drugs, antibiotics, mucus-dissolving agents (mucolytics), anti-inflammatory drugs, a pulmonary therapeutic drug, respiratory agents, immunotherapeutic drugs, gene-modifying agents, and chemo-potentiators.

11. The method of claim 2, wherein the plurality of nanoparticles is surface-associated with the gas-filled microbubble.

12. The method of claim 1, wherein the nanoparticles are spherical and have a diameter of under 800 nm and wherein the microbubbles have a diameter of from 1 to 10 µm.

13. The method of claim 1, wherein the nanoparticles are spherical and have a diameter of under 800 nm and wherein the microbubbles have a diameter of from 1 to 30 µm.

14. The method of claim 7, wherein the air-components are selected from the group consisting of: nitrogen (N2), oxygen (O2), argon (Ar), carbon dioxide (CO2), helium (He), neon (Ne) and methane (CH4).

15. The method according to claim 1, wherein the gas-filled microbubbles are prepared by
   a. providing the nanoparticles to be loaded with the medical component;
   b. adding the nanoparticles to a solution comprising a surface-active compound and/or a modifying agent;
   c. adding gas to the solution comprising the nanoparticles and the surface-active compound and/or modifying agent;
   d. mixing the solution comprising nanoparticles, a surface-active compound and/or a modifying agent, and gas to obtain gas-filled microbubbles.

16. The method according to claim 15, wherein mixing occurs from 2 seconds to 60 minutes.

17. The method according to claim 15, wherein the mixing occurs by stirring at 500 to 50,000 rpm.

18. The method according to claim 15, wherein the surface-active substance is serum, or protein or lipid or surfactant.

19. The method of claim 16, wherein mixing occurs from 1 to 10 minutes.

20. The method of claim 17, wherein mixing occurs by stirring at 1000 rpm to 30,000 rpm.

21. The method of claim 1, wherein the plurality of nanoparticles are free nanoparticles.

22. The method of claim 21, wherein the plurality of nanoparticles is coated with polyethylene glycol (PEG).

23. The method of claim 21, wherein at least one of the plurality of nanoparticles further comprises at least one targeting agent.

24. The method of claim 21, wherein the delivery system further comprises a pharmaceutically acceptable carrier.

25. The method of claim 21, wherein the gas-filled microbubble is a microbubble with nanoparticles associated on the surface.

26. The method of claim 21, wherein the medical component is selected from the group consisting of: cytotoxic/cytostatic drugs, antibiotics, mucus-dissolving agents (mucolytics), anti-inflammatory drugs, a pulmonary therapeutic drug, respiratory agents, immunotherapeutic drugs, gene-modifying agents, chemo-potentiators.

* * * * *